US006740313B2

(12) United States Patent
Forestier et al.

(10) Patent No.: US 6,740,313 B2
(45) Date of Patent: May 25, 2004

(54) COMPOSITIONS FOR GIVING THE SKIN A COLORATION SIMILAR TO THAT OF A NATURAL TAN, BASED ON A PIGMENT OF THE MONASCUS TYPE, AND USES THEREOF

(75) Inventors: Serge Forestier, Claye Souilly (FR); Didier Candau, Bievres (FR); Nathalie Seyler, Maisons-Alfort (FR); Irène Elguidj, Neuilly (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 10/270,530

(22) Filed: Oct. 16, 2002

(65) Prior Publication Data

US 2003/0133887 A1 Jul. 17, 2003

(30) Foreign Application Priority Data

Oct. 16, 2001 (FR) .............................. 01 13334
Oct. 16, 2001 (FR) .............................. 01 13335
Oct. 16, 2001 (FR) .............................. 01 13336

(51) Int. Cl.$^7$ ............................. A61K 7/42; A61K 7/44; A61K 7/00
(52) U.S. Cl. .......................... 424/59; 424/60; 424/400; 424/401
(58) Field of Search ............................ 424/59, 60, 400, 424/401

(56) References Cited

U.S. PATENT DOCUMENTS

| 4,145,254 | A |   | 3/1979  | Shepherd et al. |         |
|-----------|---|---|---------|-----------------|---------|
| 4,247,411 | A |   | 1/1981  | Vanlerberghe et al. |     |
| 4,293,543 | A |   | 10/1981 | Cotte et al.    |         |
| 5,166,355 | A | * | 11/1992 | Leistner et al. | 548/260 |
| 5,237,071 | A | * | 8/1993  | Leistner et al. | 548/259 |
| 5,627,068 | A |   | 5/1997  | Kujumdzieva et al. |      |
| 5,695,747 | A |   | 12/1997 | Forestier et al. |        |
| 5,795,565 | A |   | 8/1998  | Eteve et al.    |         |
| 5,955,060 | A |   | 9/1999  | Hüglin et al.   |         |
| 5,958,382 | A |   | 9/1999  | Vidal et al.    |         |
| 5,962,452 | A |   | 10/1999 | Haase et al.    |         |
| 5,976,512 | A |   | 11/1999 | Huber           |         |
| 6,159,455 | A |   | 12/2000 | Habeck et al.   |         |
| 6,191,301 | B1 |  | 2/2001  | Habeck et al.   |         |
| 6,238,649 | B1 |  | 5/2001  | Habeck et al.   |         |
| 6,387,355 | B2 |  | 5/2002  | Heidenfelder et al. |     |
| 6,391,289 | B2 |  | 5/2002  | Heidenfelder et al. |     |
| 6,409,995 | B1 |  | 6/2002  | Habeck et al.   |         |

FOREIGN PATENT DOCUMENTS

| DE | 197 26 184 | 12/1998 |
| DE | 197 55 649 | 6/1999  |
| DE | 198 55 649 | 6/2000  |
| DE | 100 12 408 | 9/2001  |
| EP | 0 517 104  | 12/1992 |
| EP | 0 518 772  | 12/1992 |
| EP | 0 518 773  | 12/1992 |
| EP | 0 570 838  | 11/1993 |
| EP | 0 775 698  | 5/1997  |
| EP | 0 796 851  | 9/1997  |
| EP | 0 863 145  | 9/1998  |
| EP | 0 878 469  | 11/1998 |
| EP | 0 893 119  | 1/1999  |
| EP | 0 903 342  | 3/1999  |
| EP | 0 933 376  | 8/1999  |
| EP | 0 967 200  | 12/1999 |
| EP | 1 046 391  | 10/2000 |
| EP | 1 133 981  | 9/2001  |
| FR | 2 315 991  | 1/1977  |
| FR | 2 416 008  | 8/1979  |
| FR | 2 466 492  | 4/1981  |
| GB | 2 303 549  | 2/1997  |
| JP | 57-145159  | 9/1982  |
| JP | 50-149512  | 8/1985  |
| JP | 4-23880    | 1/1992  |
| JP | 10-194928  | 7/1998  |
| WO | WO 93/04665 | 3/1993 |
| WO | WO 97/35842 | 10/1997 |
| WO | WO 01/43711 | 6/2001  |

OTHER PUBLICATIONS

Patent Abstracts of Japan, vol. 016, No. 054 (C–0909), Feb. 12, 1992 & JP 03 254686 A.
Database WPI, Section Ch, Week 198920, Derwent Publications Ltd., London, GB; Class D16, An 1989–147359, XP00220778 & JP 01 090109 A.
Database WPI, Section Ch, Week 199840, Derwent Publications Ltd., London, GB; Class D21, AN 1998–462741, XP0022007789 & JP 10 194928 A.
P. Juzlová et al., "Secondary metabolites of the fungus Monascus: a review," Journal of Industrial Microbiology, vol. 16, 1996, pp. 163–170.
A.D. Bangham et al., "Diffusion of Univalent Ions Across the Lamellae of Swollen Phopholipids," Journal of Molecular Biology, vol. 13, 1965, pp. 238–252.
English language Derwent Abstract of DE 197 26 184 Dec. 24, 1998.
English language Derwent Abstract of FR 2 315 991, Jan. 28, 1977.
English language Derwent Abstract of JP 57–145159, Sep. 8, 1982.
English language Derwent Abstract of JP 60–149512, Aug. 7, 1985.
English language Derwent Abstract of JP 4–23880, Jan. 28, 1992.
English language Derwent Abstract of JP 10–194928, Jul. 28, 1998.

* cited by examiner

*Primary Examiner*—Shelley A. Dodson
(74) *Attorney, Agent, or Firm*—Finnegan, Henderson, Farabow, Garrett & Dunner, L.L.P.

(57) ABSTRACT

A cosmetic and/or dermatological composition that produces on the skin a long-lasting and non-covering coloration similar to that of a natural tan comprising, in a cosmetically acceptable medium, at least one pigment, which may be obtained by extraction with an organic or aqueous-organic solvent of a culture medium of micromycetes of the Monascus type, as well as the use of the composition for giving the skin a long-lasting and non-covering coloration similar to that of naturally tanned skin.

37 Claims, No Drawings

COMPOSITIONS FOR GIVING THE SKIN A COLORATION SIMILAR TO THAT OF A NATURAL TAN, BASED ON A PIGMENT OF THE MONASCUS TYPE, AND USES THEREOF

The present invention relates to a cosmetic and/or dermatological composition that can produce on skin a long-lasting and non-covering coloration similar to that of a natural tan, comprising, in a cosmetically acceptable medium, at least one pigment, which may be obtained by extraction with a solvent chosen from organic and aqueous-organic solvents of a culture medium of micromycetes of the Monascus type.

The invention also relates to the use of the composition for giving the skin a coloration similar to that of naturally tanned skin.

Nowadays, it is important to look healthy, and tanned skin is always a sign of good health. However, a natural tan is not always desirable because it requires long exposure to UV radiation, for example, UV-A radiation, which causes the tanning of the skin but may induce an adverse change therein, such as in sensitive skin or skin that is continually exposed to solar radiation. It is therefore desirable to find an alternative to a natural tan that is compatible with the requirements of such skin types.

Most of the cosmetic products intended for artificially tanning the skin are based on carbonyl derivatives which, by interacting with the amino acids in the skin, allow the formation of coloured products.

It is known that dihydroxyacetone (DHA) is an advantageous product which is commonly used in cosmetics as an agent for artificially tanning the skin; when applied to the skin, such as to the face, it can give a tanning or bronzing effect which is similar in appearance to that which may result from prolonged exposure to sunlight (a natural tan) or light from a UV lamp.

One drawback of DHA is the length of time the coloration takes to develop: for example, several hours (3 to 5 hours in general) can be required for the coloration to be revealed. There is thus an increasing demand for self-tanning products that can act quickly and can give a coloration that is closer to that of a natural tan.

Therefore, efforts are still underway to find novel compounds and novel compositions which can give the skin an artificial coloration close to that of a natural tan in a simple, effective, fast, and risk-free manner.

The pigments derived from filamentous fungi of the Monascus type have long been known as colouring agents for food products, pharmaceutical products, and cosmetics. Filamentous fungi of the Monascus type are obtained by fermentation. The strains usually used are the strains of the genus *Monascus anka, Monascus purpurea, Monascus ruber* and *Monascus pilosus,* all of which are readily available. These pigment-forming micromycetes produce six types of pigments which differ in their degree of unsaturation, their auxochromic functions, and the size of their aliphatic chain. These pigments may be intracellular or extracellular and can have different shades depending on their chemical structure. Distinguished pigments include, for example, yellow pigments of the ankaflavin type and of the monascin type; orange pigments of the monoascorubrin and rubropunctatin types; and red pigments of the monoascorubramine and rubropunctamine types. The orange pigments can be derived directly from the secondary metabolism of the fungus, whereas the yellow pigments and red pigments are metabolites derived from a reduction reaction of the orange pigments to obtain the yellow pigments, and an amination reaction of the orange pigments to obtain the red pigments.

Patent document JP 04-023880 discloses cosmetic compositions containing an extract derived from the mutant strain R300-30 from *Monascus anka* (FERM No. 11135) and optionally other standard UV screening agents; the extract is used for its UVA- and UVB-absorbing properties. This document does not mention the use of these compositions for artificially colouring the skin.

Patent document JP 64-90109 discloses cosmetic compositions containing a liquid extract of a culture of a mould of the genus Monascus. This liquid extract contains proteolytic enzymes, vitamins, peptides and various amino acids. These compositions are used for their moisturizing and detergent properties on the skin.

Patent documents JP 60-149 512 and JP 10-194928 disclose makeup compositions containing Monascus pigments linked to a regenerated silk fibroin powder. These documents do not mention the use of these compositions for artificially colouring the skin.

Patent document JP 57-145 159 discloses cosmetic facial care compositions based on natural pigments (for example Monascus) associated with a porous magnesium and/or calcium aluminate silicate powder. This document does not mention the use of these compositions for artificially colouring the skin.

Patent document WO 01/43711 discloses skincare compositions containing a combination of an extract of Monascus and an ascorbic acid derivative (palmitate ascorbyl, sodium ascorbyl or phosphate ascorbyl) or a retinol derivative (retinal or an ester thereof). These compositions are used for their regulatory activity on skin sebum, their stimulatory activity on collagen synthesis by the skin fibroblasts, and their phytooestrogenic properties. This document does not mention the use of these compositions for artificially colouring the skin.

After considerable research conducted in the field of artificial colouring of the skin, the inventors have now discovered that the inclusion, as a skin-colouring agent, of at least one pigment that may be obtained by extraction with a solvent chosen from organic and aqueous-organic solvents of a culture medium of micromycetes of the Monascus type in, or for the manufacture of, a cosmetic and/or dermatological composition makes it possible to give the skin, very soon after the composition has been applied thereto, a long-lasting and non-covering coloration close to that of a natural tan.

One aspect of the present invention is thus a cosmetic and/or dermatological composition that can produce on the skin a long-lasting and non-covering coloration similar to that of a natural tan, comprising, in a cosmetically acceptable medium, at least one pigment which may be obtained by extraction with a solvent chosen from organic and aqueous-organic solvents of a culture medium of micromycetes of the Monascus type.

Another aspect of the invention is the inclusion of at least one pigment that may be obtained by extraction with a solvent chosen from organic and aqueous-organic solvents of a culture medium of micromycetes of the Monascus type, in, or for the manufacture of, a cosmetic composition, with the purpose of giving the skin a long-lasting and non-covering coloration close to that of a natural tan.

Another aspect of the present invention is a process for giving the skin a long-lasting and non-covering coloration similar to that of a natural tan, comprising applying to the skin an effective amount of at least one pigment which may be obtained by extraction with a solvent chosen from organic and aqueous-organic solvents of a culture medium of micromycetes of the Monascus type in a cosmetic composition containing it.

The composition and the process in accordance with the invention make it possible to obtain an artificial coloration close to that of a natural tan in a short amount of time. Thus, an immediate coloration can be obtained, which can allow visualization of the application and consequently visualization of better homogeneity in the spreading of the composition on the skin and thus visualization of the resulting coloration. Furthermore, the artificial coloration obtained on the skin according to the invention can be extremely close to that of a natural tan.

In accordance with the present invention, the expression "composition that produces on the skin a long-lasting and non-covering coloration similar to that of a natural tan" means a formulation with an affinity for the skin which allows it to give the skin a coloration, which is not removed either with water or with a solvent, and which withstands both rubbing and washing with a solution containing surfactants; and a coloration, which does not have a tendency to opacify the skin.

Such a long-lasting and non-covering coloration is thus distinguished from the superficial, transient, and opacifying coloration provided, for example, by a makeup product.

The coloration close to that of naturally tanned skin may be determined by an in vitro test on a support of the Vitro-Skin® type. Vitro-Skin® is a support developed for research which reproduces the properties of the surface of human skin. It contains both optimized protein and optimized lipid components and it is designed with a topography, a pH, a critical surface tension, and an ionic strength similar to those of human skin. Vitro-Skin® is supplied by IMS (IMS Testing Group, USA).

Other characteristics, aspects, and advantages of the present invention will become apparent on reading the detailed description which follows.

The compositions in accordance with the present invention generally comprise at least one pigment that may be obtained by extraction with a solvent chosen from organic and aqueous-organic solvents of a culture medium of micromycetes of the Monascus type in a sufficient amount to make it possible to obtain, 15 minutes after application to a support of the Vitro-Skin® type at a concentration of 2 mg/cm$^2$, a darkening characterized in a (L*, a*, b*) colorimetric measuring system by a ΔL* ranging from −0.5 to −20. For example, ΔL* may range from −0.5 to −15.

The compositions in accordance with the present invention give, 15 minutes after application to a support of the Vitro-Skin® type at a concentration of 2 mg/cm$^2$, a coloration defined in the (L*, a*, b*) colorimetric measuring system, by a ratio Δa*/Δb* ranging from 0.5:1 to 6:1, and further for example ranging from 0.8:1 to 6:1.

In the (L*, a*, b*) colorimetric measuring system:

L* represents the luminance or clarity, a* represents the red-green axis (−a*=green, +a*=red) and b* represents the yellow-blue axis (−b*=blue, +b*=yellow). Thus, a* and b* express the shade of the skin.

ΔL* reflects the darkening of the colour: the more negative the ΔL*, the darker the colour becomes, wherein:

ΔL*=L* uncoloured support−L* coloured support

The ratio Δa*/Δb* reflects the red/yellow balance and thus the shade, wherein:

Δa*=a* uncoloured support−a* coloured support
Δb*=b* uncoloured support−b* coloured support Among the pigments derived from the genus Monascus which may be used according to the present invention mention may be made of:

(i) The yellow pigments corresponding to one of the formulae (Ia), (Ib) and (Ic) below:

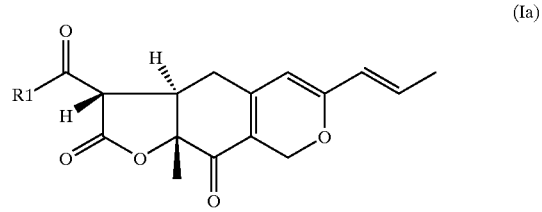

(Ia)

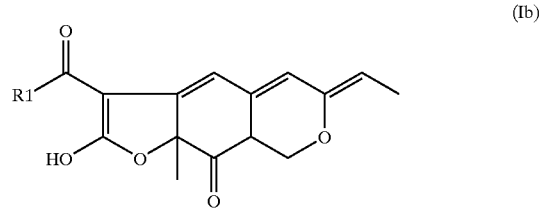

(Ib)

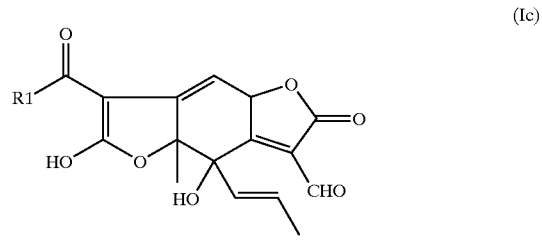

(Ic)

wherein, in each formula, R1 is chosen from a hydrogen atom and linear and branched $C_1$–$C_{10}$ alkyl radicals.

For example:

pigments of formula (Ia) are those wherein R1 is chosen from linear $C_5$ alkyl (monascin) and linear $C_7$ alkyl (ankaflavin) radicals, pigments of formula (Ib) and of formula (Ic) are those wherein, R1 is chosen from linear $C_5$ and $C_7$ alkyl radicals, for example those described and prepared in an article by P. Juzlova, L. Martinkova, & V. Kren, *Secondary Metabolites of the Fungus Monascus: A Review*, 16 JOURNAL OF INDUSTRIAL MICROBIOLOGY 163–170 (1996).

(ii) The orange pigments of formula (II) below:

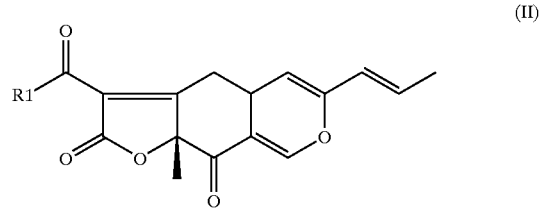

(II)

wherein, R1 is chosen from a hydrogen atom and linear and branched $C_1$–$C_{10}$ alkyl radicals.

For example, the pigments of formula (II) are those wherein, R1 is chosen from linear $C_5$ alkyl (rubropunctatin) and linear $C_7$ alkyl (monascorubrin) radicals.

(iii) The red pigments of formula (III) below:

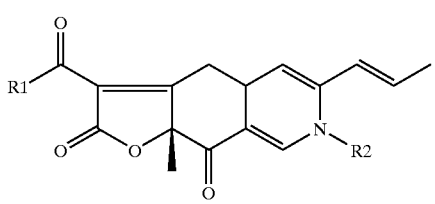

(III)

wherein, R1 is chosen from a hydrogen atom and linear and branched $C_1$–$C_{10}$ alkyl radicals, R2 is chosen from a hydrogen atom and linear and branched $C_1$–$C_{30}$ alkyl radicals, said alkyl radicals optionally being substituted with at least one entity chosen from carboxylic acids, sulphonic acids, amine functional groups, and rings comprising from 4 to 10 carbon atoms.

For example, the pigments of formula (III) wherein, R1 is chosen from linear $C_5$ alkyl and linear $C_7$ alkyl radicals may be used.

Among these red pigments, mention may be made of those wherein, R2 is an amino acid residue, for example, the pigments of the N-glutaryl monoascorubramine, N-acetyl monoascorubramine and N-acetyl rubropunctamine types.

Among these red pigments mention may also be made of those wherein, R2 is a hydrogen atom, for example, rubropunctamine and monoascorubramine.

The pigments in accordance with the invention can be obtained by extraction with a solvent chosen from organic and aqueous-organic solvents of a culture medium of filamentous fungi of the genus Monascus produced by fermentation. Two types of fermentation process may be used: fermentation in liquid medium or fermentation in solid medium according to the processes as described in patent documents U.S. Pat. No. 4,145,254, JP 10 194 928 and JP 04-023880 which are incorporated herein by reference. The extraction of these media using a solvent chosen from organic and aqueous-organic solvents can produce pigments free of any protein substances such as proteins, peptides, and enzymes. The extraction solvent comprises at least one organic solvent, and may optionally comprise water. The organic solvents used may be chosen from alcohols, for example, ethanol, methanol, normal primary propyl alcohol, isopropyl alcohol, normal primary butyl alcohol, propylene glycol, and glycerol. The organic solvents may also be chosen from, for example, diethyl ether, acetone, ethyl methyl ketone, and ethyl acetate. The organic solvents used may further be chosen from supercritical fluids and fluorinated solvents, for example, dodecafluoropentane, tetradecafluorohexane, perfluorinated N-methylmorpholine, and methoxynonafluorobutane.

The strains producing such pigments may be chosen from those of the type *Monascus purpureus, Monascus ruber, Monascus major, Monascus rubiginosus, Monascus species,* and *Monascus anka,* and, for example:

*Monascus purpureus*
CCM 8152
CCM 8152/10
ATCC 16365
ATCC 6405
ATCC 16427
NBIMC 23255 (94-25)
IFO 4513
OUT 2013
OUT 2014
*Monascus ruber*
CCM 8111
CCM 8112
ATCC 96218
DSM 62748
*Monascus major*
ATCC 16362
*Monascus rubiginosus*
ATCC 16367
*Monascus species*
ATCC 16435
*Monascus anka*
ATCC 16360
IFO 6540
IAM 8002
IFO 4473.

The pigments according to the invention are chosen from, for example, the red pigments of formula (III) as defined above, and further, for example, an aqueous-alcoholic extract of *Monascus anka* atomized onto maltodextrin (4 parts *Monascus anka*/96 parts maltodextrin), such as the commercial product Monacolor MS-60 from Ichimaru Pharcos.

The concentration of the pigment derived from Monascus as described above in accordance with the present invention ranges, for example, from 0.0001% to 10%, further for example, from 0.001% to 5% by weight relative to the total weight of the composition.

According to one embodiment of the invention, the pigment derived from Monascus in the composition of the invention is different from an extract obtained from the mutant strain R300-30 of *Monascus anka* (FERM No. 11135) as disclosed in patent document JP 04-023880.

According to another aspect of the invention, the Monascus pigment is not linked to a regenerated silk fibroin powder as found in the patent documents JP 60-149512 and JP 10-19492, or to a porous magnesium and/or calcium aluminate silicate as found in the patent document JP 57-145159.

According to another aspect of the invention, the composition of the invention does not contain an ascorbic acid derivative or a retinol derivative as do the compositions described in the patent document WO 01/43711.

The composition in accordance with the present invention may further comprise at least one self-tanning agent chosen from mono- and polycarbonyl self-tanning agents.

The mono- and polycarbonyl self-tanning agents are chosen, for example, from isatin, alloxan, ninhydrin, glyceraldehyde, mesotartaricaldehyde, glutaraldehyde, erythrulose, pyrazoline-4,5-dione derivatives as described in patent documents FR 2 466 492 and WO 97/35842, dihydroxyacetone (DHA), 4,4-dihydroxypyrazolin-5-one derivatives as described in patent document EP 903 342, these self-tanning agents possibly being combined with direct dyes or indole derivatives.

For example, dihydroxyacetone (DHA) can be used as the self-tanning agent in one embodiment of the invention.

The at least one self-tanning agent chosen from mono- and polycarbonyl self-tanning agents is generally present in the composition according to the invention in an amount ranging, for example, from 0.1% to 10% by weight relative to the total weight of the composition and further, for example, ranging from 0.2% to 8% by weight relative to the total weight of the composition.

The composition in accordance with the present invention may further comprise at least one additional agent chosen from organic and mineral agents for screening out ultraviolet radiation.

The organic UV screening agents in accordance with the invention may be water-soluble, liposoluble, or insoluble in the usual cosmetic solvents. They are chosen, for example, from anthranilates, cinnamic derivatives, dibenzoylmethane derivatives, salicylic derivatives, camphor derivatives, triazine derivatives such as those described in patent documents U.S. Pat. No. 4,367,390, EP 863 145, EP 517 104, EP 570 838, EP 796 851, EP 775 698, EP 878 469, EP 933 376 and benzophenone derivatives, for example, those described in patent documents EP-A-1 046 391 and DE 100 12 408, benzalmalonate derivatives, β,β'-diphenylacrylate derivatives, benzotriazole derivatives, benzimidazole derivatives, imidazolines, bis-benzazolyl derivatives as described in patent documents EP 669 323 and U.S. Pat. No. 2,463,264, p-aminobenzoic acid (PABA) derivatives, methylenebis(hydroxyphenyl)benzotriazole derivatives as described in patent documents U.S. Pat. Nos. 5,237,071, 5,166,355, GB 2 303 549, DE 197 26 184, and EP 893 119, screening polymers and screening silicones such as those described, for example, in patent document WO 93/04665, dimers derived from α-alkylstyrene, such as those described in patent document DE 198 55 649, 4,4-diarylbutadiene derivatives such as those described in patent documents EP 0 967 200, DE 197 55 649, and EP 1133981, and mixtures thereof.

Examples of the organic screening agents include, but are not limited to those below under their INCI names:

para-Aminobenzoic acid derivatives:
  PABA,
  Ethyl PABA,
  Ethyl dihydroxypropyl PABA,
  Ethylhexyl dimethyl PABA sold, for example, under the name "Escalol 507" by ISP,
  Glyceryl PABA,
  PEG-25 PABA sold under the name "Uvinul P25" by BASF;
Salicylic derivatives:
  Homosalate sold under the name "Eusolex HMS" by Rona/EM Industries,
  Ethylhexyl salicylate sold under the name "Neo Heliopan OS" by Haarmann and Reimer,
  Dipropylene glycol salicylate sold under the name "Dipsal" by Scher,
  TEA salicylate sold under the name "Neo Heliopan TS" by Haarmann and Reimer;
Dibenzoylmethane derivatives:
  Butyl methoxydibenzoylmethane sold, for example, under the trade name "Parsol 1789" by Hoffmann LaRoche,
  Isopropyldibenzoylmethane;
Cinnamic derivatives:
  Ethylhexyl methoxycinnamate sold, for example, under the trade name "Parsol MCX" by Hoffmann LaRoche,
  Isopropyl methoxycinnamate,
  Isoamyl methoxycinnamate sold under the trade name "Neo Heliopan E 1000" by Haarmann and Reimer,
  Cinoxate,
  DEA methoxycinnamate,
  Diisopropyl methylcinnamate
  Glyceryl ethylhexanoate dimethoxycinnamate;
β,β'-Diphenyl acrylate derivatives:
  Octocrylene sold, for example, under the trade name "Uvinul N539" by BASF
  Etocrylene sold, for example, under the trade name "Uvinal N35" by BASF;

Benzophenone derivatives:
Benzophenone-1 sold under the trade name "Uvinul 400" by BASF,
Benzophenone-2 sold under the trade name "Uvinul D50" by BASF,
Benzophenone-3 or Oxybenzone sold under the trade name "Uvinul M40" by BASF,
Benzophenone-4 sold under the trade name "Uvinul MS40" by BASF,
Benzophenone-5,
Benzophenone-6 sold under the trade name "Helisorb 11" by Norquay,
Benzophenone-8 sold under the trade name "Spectra-Sorb UV-24" by American Cyanamid,
Benzophenone-9 sold under the trade name "Uvinul DS-49" by BASF,
Benzophenone-12,
n-Hexyl 2-(4-diethylamino-2-hydroxybenzoyl)benzoate;
Benzylidenecamphor derivatives:
3-Benzylidenecamphor manufactured under the name "Mexoryl SD" by Chimex,
4-Methylbenzylidenecamphor sold under the name "Eusolex 6300" by Merck,
Benzylidenecamphorsulphonic acid manufactured under the name "Mexoryl SL" by Chimex,
Camphor benzalkonium methosulphate manufactured under the name "Mexoryl SO" by Chimex,
Terephthalylidenedicamphorsulphonic acid manufactured under the name "Mexoryl SX" by Chimex,
Polyacrylamidomethylbenzylidenecamphor manufactured under the name "Mexoryl SW" by Chimex;
Phenylbenzimidazole derivatives:
Phenylbenzimidazolesulphonic acid sold, for example, under the trade name "Eusolex 232" by Merck,
Disodiumphenyldibenzimidazole tetrasulphonate sold under the trade name "Neo Heliopan AP" by Haarmann and Reimer;
Triazine derivatives:
Anisotriazine sold under the trade name "Tinosorb S" by Ciba Geigg,
Ethylhexyltriazone sold, for example, under the trade name "Uvinul T150" by BASF,
Diethylhexylbutamidotriazone sold under the trade name "Uvasorb HEB" by Sigma 3V,
2,4,6-Tris(diisobutyl 4'-aminobenzalmalonate) s-triazine;
Phenylbenzotriazole derivatives:
Drometrizole trisiloxane sold under the name "Silatrizole" by Rhodia Chimie,
Methylenebis(benzotriazolyl)tetramethylbutylphenol sold in solid form under the trade name "MIXXIM BB/100" by Fairmount Chemical, or in micronized form as an aqueous dispersion under the trade name "Tinosorb M" by Ciba Specialty Chemicals;
Anthranilic derivatives:
Menthyl anthranilate sold under the trade name "Neo Heliopan MA" by Haarmann and Reimer;
Imidazoline derivatives:
Ethylhexyldimethoxybenzylidenedioxoimidazoline propionate;
Benzalmalonate derivatives:
Polyorganosiloxane containing benzalmalonate functions, sold under the trade name "Parsol SLX" by Hoffmann LaRoche;

4,4-arylbutadiene derivatives 1,1-dicarboxy(2,2-dimethyl-propyl)-4,4-diphenylbutadiene;

and mixtures thereof.

The organic UV screening agents further, for example, are chosen from the following compounds:

Ethylhexyl salicylate,

Butyl methoxydibenzoylmethane,

Ethylhexyl methoxycinnamate,

Octocrylene,

Phenylbenzimidazolesulphonic acid,

Terephthalylidenedicamphorsulphonic acid,

Benzophenone-3,

Benzophenone-4,

Benzophenone-5,

4-Methylbenzylidenecamphor,

Disodiumphenyldibenzimidaloe tetrasulphonate,

Anisotriazine,

Ethylhexyltriazone,

Diethylhexylbutamidotriazone, 2,4,6-tris(diisobutyl 4'-aminobenzalmalonate)-s-triazine, Methylenebis(benzotriazolyl)tetramethylbutylphenol, n-Hexyl 2-(4-diethylamino-2-hydroxybenzoyl)benzoate, 1,1-dicarboxy(2,2'-dimethyl-propyl)-4,4-diphenylbutadiene, Drometrizole trisiloxane, and mixtures thereof.

The mineral screening agents are generally pigments or nanopigments of coated or uncoated metal oxides. The average size of the primary particles of those pigments or nanopigments generally ranges, for example, from 5 to 100 nm, and further, for example, from 10 nm to 50 nm. Such particle size can readily be determined by one of ordinary skill in the art using known techniques. For example, the nanopigments may be chosen from nanopigments of titanium oxide (amorphous or crystallized in rutile and/or anatase form), of iron oxide, of zinc oxide, of zirconium oxide, and of cerium oxide, which are all UV stabilizers that are well known in the art. Conventional coating agents may also be, for example, chosen from alumina and aluminium stearate. Such coated or uncoated metal oxide nanopigments are disclosed, for example, in patent documents EP-A-0 518 772 and EP-A-0 518 773.

The radiation-screening agents in accordance with the invention are generally present in the composition in an amount ranging from 0.1% to 20% by weight relative to the total weight of the composition, for example, ranging from 0.2% to 15% by weight relative to the total weight of the composition.

The composition according to the present invention may also comprise at least one conventional cosmetic adjuvant chosen, for example, from fatty substances, organic solvents, ionic and non-ionic thickeners, softeners, antioxidants, free-radical scavengers, opacifiers, stabilizers, emollients, silicones, α-hydroxy acids, insect repellents, antifoams, moisturizers, vitamins, fragrances, preserving agents, surfactants, fillers, polymers, propellants, acidifying and basifying agents, colorants and any other ingredient usually used in cosmetics and/or dermatology, for example, for manufacturing anti-sun compositions in the form of emulsions.

The fatty substances comprise at least one ingredient chosen from oils and waxes. The term "oil" means a compound that is liquid at room temperature. The term "wax" means a compound that is solid or substantially solid at room temperature with a melting point that is generally greater than 35° C. The fatty substances further comprise fatty acids, fatty alcohols, and fatty acid esters, which may be linear or cyclic, such as benzoic, trimellitic, and hydroxybenzoic acid derivatives.

Oils, for example, include, but are not limited to, mineral oils (paraffin), plant oils (sweet almond oil, macadamia oil, blackcurrant seed oil, jojoba oil), synthetic oils such as perhydrosqualene, fatty alcohols, fatty acids and fatty esters (such as the $C_{12}$–$C_{15}$ alkyl benzoate sold under the trade name "Finsolv TN" by the company Finetex, octyl palmitate, isopropyl lanolate, and triglycerides including those of capric/caprylic acid), oxyethylenated or oxypropylenated fatty esters and ethers, silicone oils (cyclomethicone, polydimethylsiloxanes and PDMSs), fluoro oils, and polyalkylenes.

Waxy compounds, for example, include, but are not limited to, paraffin, carnauba wax, beeswax, and hydrogenated castor oil.

Among the organic solvents, mention may be made of lower alcohols and polyols.

The thickeners may be chosen, for example, from crosslinked polyacrylic acids, modified and unmodified guar gums, and celluloses, such as hydroxypropyl guar gum, methylhydroxyethylcellulose, and hydroxypropylmethylcellulose.

A person skilled in the art will take care to select the optional additional compound(s) mentioned above and/or the amounts thereof such that the advantageous properties intrinsically associated with the use of pigments in accordance with the invention are not, or are not substantially, adversely affected by the addition(s) envisaged.

The composition according to the invention may be prepared according to the techniques that are well known to those skilled in the art, for example, those intended for preparing oil-in-water or water-in-oil emulsions.

The composition according to the invention may be, for example, in the form of a simple or complex (O/W, W/O, O/W/O or W/O/W) emulsion such as a cream or a milk, a gel or a cream-gel, a lotion, a powder or a solid tube, and may optionally be conditioned as an aerosol, and may be in the form of a mousse or spray.

The composition according to the invention may be, for example, in the form of an oil-in-water or water-in-oil emulsion.

When it is an emulsion, the aqueous phase of this emulsion may comprise a non-ionic vesicular dispersion prepared according to known processes (Bangham, Standish & Watkins, 13 J. MOL. BIOL. 238 (1965); FR 2 315 991 and FR 2 416 008).

Non-limiting examples illustrating the invention are as follows:

EXAMPLE 1

The following compositions were prepared (the amounts are expressed as weight percentages relative to the total weight of the composition):

| Composition $A_1$ (not in accordance with the invention): | |
|---|---|
| Dihydroxyacetone (DHA) | 1.00 g |
| Absolute ethanol | 49.50 g |

-continued

| | |
|---|---|
| Propylene glycol | 24.75 g |
| Demineralized water | 24.75 g |
| Composition B₁ (in accordance with the invention) | |
| *Monascus anka* pigment | 1.00 g |
| (Monacolor MS-60 from Ichimura Pharcos) | |
| Absolute ethanol | 49.50 g |
| Propylene glycol | 24.75 g |
| Demineralized water | 24.75 g |

Evaluation protocol:

Preparation of VitroSkin®

VitroSkin® must be hydrated beforehand in order to be used in the in vitro colour characterization test.

Preparing the Hydration Liquid

The bottom of a desiccator was filled with a water/glycerol mixture in the proportion of 70/30.

Hydration of VitroSkin®

Squares of VitroSkin® cut up beforehand were placed on a support in the closed desiccator containing the hydration liquid. A period of 16 hours of hydration is necessary to use the VitroSkin®.

Compositions $A_1$ and $B_1$ were then applied to the VitroSkin® squares taken from the desiccator, at a concentration of 2 mg/cm² over an area of 2.5×2.5 cm².

The following five series of colorimetric measurements were carried out using a Minolta CM-508d colorimeter:

1) before application of the composition, and
2) 15 minutes after the application.

The results are expressed in the system (L*, a*, b*) wherein, L* represents the luminance, a* represents the red-green axis (−a*=green, +a*=red), and b* represents the yellow-blue axis (−b*=blue, +b*=yellow). Thus, a* and b* express the shade of the skin.

To evaluate the coloration intensity, the value of interest is ΔL*, which reflects the darkening of the colour: the more negative the value of ΔL*, the more the colour is darkened, wherein:

$\Delta L^* = L^*$ uncoloured VitroSkin® $- L^*$ coloured VitroSkin®

For the shade of the coloration obtained, the value of interest is the ratio Δa*/Δb*, which reflects the red/yellow equilibrium, wherein:

$\Delta a^* = a^*$ uncoloured VitroSkin® $- a^*$ coloured VitroSkin®

$\Delta b^* = b^*$ uncoloured VitroSkin® $- b^*$ coloured VitroSkin®

The results obtained are collected in Table (I) below:

TABLE (I)

| | Composition A₁ (not in accordance with the invention) | Composition B₁ (in accordance with the invention) |
|---|---|---|
| ΔL* | −0.99 | −8.4 |
| Δa*/Δb* | 0.06:1 | 5.8:1 |

It was thus found that, 15 minutes after the application of composition $A_1$ containing DHA as skin-colouring agent, the VitroSkin® had only a very faint coloration, because the DHA had not yet had the time to act (ΔL*=−0.99). On the other hand, composition $B_1$ according to the invention made it possible to obtain immediately a coloration of good intensity on the VitroSkin® (ΔL*=−8.4).

EXAMPLE 2

The following compositions were prepared (the amounts are expressed as weight percentages relative to the total weight of the composition):

| | |
|---|---|
| Composition A₂ (not in accordance with the invention): | |
| Dihydroxyacetone (DHA) | 1.00 g |
| Absolute ethanol | 49.50 g |
| Propylene glycol | 24.75 g |
| Demineralized water | 24.75 g |
| Composition B₂ (in accordance with the invention) | |
| Red *Monascus anka* pigment | 1.00 g |
| (Monacolor MS-60 from Ichimaru Pharcos) | |
| Dihydroxyacetone (DHA) | 1.00 g |
| Absolute ethanol | 49.2 g |
| Propylene glycol | 24.4 g |
| Demineralized water | 24.4 g |

Same type of tests as those described in example 1 were carried out.

The results obtained are collected in Table (II) below:

TABLE (II)

| | Composition A₂ (not in accordance with the invention) | Composition B₂ (in accordance with the invention) |
|---|---|---|
| ΔL* | −0.99 | −7.8 |
| Δa*/Δb* | 0.06:1 | 4.2:1 |

It was thus found that, 15 minutes after the application of composition $A_2$ containing DHA as skin-colouring agent, only a very faint coloration was found on Vitro Skin®, because the DHA had not yet had the time to act (ΔL*=−0.99). On the other hand, composition $B_2$ according to the invention made it possible to obtain immediately a coloration of good intensity on the VitroSkin® (ΔL*=−7.8).

EXAMPLE 3

The following compositions were prepared (the amounts are expressed as weight percentages relative to the total weight of the composition):

| | |
|---|---|
| Composition A₃ (not in accordance with the invention): | |
| Dihydroxyacetone (DHA) | 1.00 g |
| Absolute ethanol | 49.50 g |
| Propylene glycol | 24.75 g |
| Demineralized water | 24.75 g |
| Composition B₃ (in accordance with the invention) | |
| Monascus pigment | 1.00 g |
| (Monascus Red from the Kunming botanical institute) | |
| Terephthalylidenedicamphorsulphonic acid | 0.5 g |
| Absolute ethanol | 49.3 g |
| Propylene glycol | 24.6 g |
| Demineralized water | 24.6 g |

The same type of tests as those described in example 1 were carried out.

The results obtained are collected in Table (III) below:

TABLE (III)

|  | Composition A₃ (not in accordance with the invention) | Composition B₃ (in accordance with the invention) |
|---|---|---|
| ΔL* | −0.99 | −10.64 |
| Δa*/Δb* | 0.06:1 | 4.6:1 |

It was found that, 15 minutes after the application of composition $A_3$ containing DHA as skin-colouring agent, the VitroSkin® had only a very faint coloration, because the DHA had not yet had the time to act ($\Delta L^* = -0.99$). On the other hand, composition $B_3$ according to the invention made it possible to obtain immediately a coloration of good intensity on the VitroSkin® ($\Delta L^* = -10.64$).

What is claimed is:

1. A cosmetic and/or dermatological composition that produces on skin a long-lasting and non-covering coloration similar to that of a natural tan comprising, in said composition, a cosmetically acceptable medium and at least one pigment, which may be obtained by extraction with a solvent chosen from organic and aqueous-organic solvents of a culture medium of Monascus micromycetes.

2. The composition according to claim 1, wherein said at least one pigment is in an effective amount to obtain, 15 minutes after applying the composition onto a VitroSkin® support at a concentration of 2 mg/cm², a darkening characterized in a L*a*b* colorimetric measuring system by a ΔL* ranging from −0.5 to −20.

3. The composition according to claim 2, wherein the ΔL* ranges from −0.5 to −15.

4. The composition according to claim 2, wherein said at least one pigment is present in an amount that is effective to obtain, 15 minutes after applying the composition to a VitroSkin® support at a concentration of 2 mg/cm², a coloration defined in the L*a*b* colorimetric system by a ratio Δa*/Δb* ranging from 0.5:1 to 6:1.

5. The composition of claim 4, wherein the ratio Δa*/Δb* ranges from 0.8:1 to 6:1.

6. A cosmetic and/or dermatological composition that produces on skin a long-lasting and non-covering coloration similar to that of a natural tan comprising, in said composition, a cosmetically acceptable medium and at least one pigment chosen from yellow pigments corresponding to one of the formulae (Ia), (Ib), and (Ic) below:

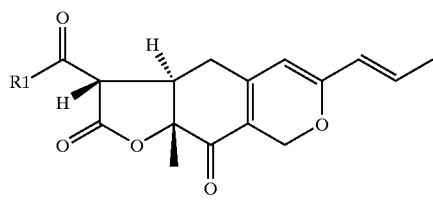

(Ia)

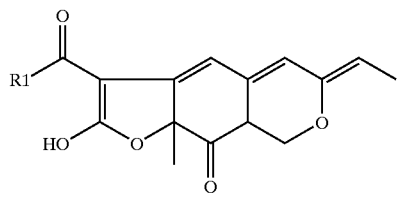

(Ib)

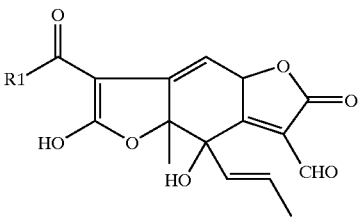

(Ic)

wherein, in each formula, R1 is chosen from a hydrogen atom and linear and branched $C_1$–$C_{10}$ alkyl radicals.

7. The composition according to claim 6, wherein the at least one pigment is chosen from:
the pigments of formula (Ia), wherein R1 is chosen from linear $C_5$ and $C_7$ alkyl radicals;
the pigments of formula (Ib), wherein R1 is chosen from linear $C_5$ and $C_7$ alkyl radicals; and
the pigments of formula (Ic), wherein R1 is chosen from linear $C_5$ and $C_7$ alkyl radicals.

8. The composition according to claim 7, wherein the at least one pigment is chosen from monascin and ankaflavin.

9. A cosmetic and/or dermatological composition that produces on skin a long-lasting and non-covering coloration similar to that of a natural tan comprising, in said composition, a cosmetically acceptable medium and at least one pigment chosen from orange pigments of formula (II) below:

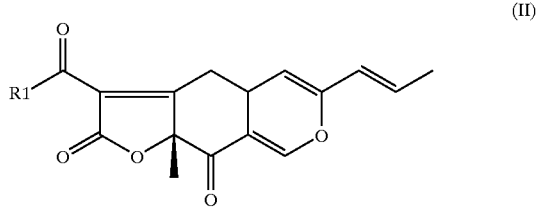

(II)

wherein R1 is chosen from a hydrogen atom and $C_1$–$C_{10}$ alkyl radicals.

10. The composition according to claim 9, wherein the at least one pigment is chosen from orange pigments of formula (II) wherein R1 is chosen from linear $C_5$ and $C_7$ alkyl radicals.

11. The composition according to claim 10, wherein the at least one pigment is chosen from rubropunctatin and monascorubrin.

12. A cosmetic and/or dermatological composition that produces on skin a long-lasting and non-covering coloration similar to that of a natural tan comprising, in said composition, a cosmetically acceptable medium and at least one pigment chosen from red pigments of formula (III) below:

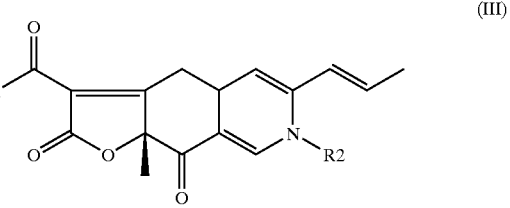

(III)

wherein R1 is chosen from a hydrogen atom and linear and branched $C_1$–$C_{10}$ alkyl radicals, R2 is chosen from a hydrogen atom and linear and branched $C_1$–$C_{30}$ alkyl radicals, said alkyl radicals optionally being substituted with at least one entity chosen from carboxylic acids, sulphonic acids, and amine functional groups and rings comprising from 4 to 10 carbon atoms.

13. The composition according to claim 12, wherein the at least one pigment is chosen from the red pigments of formula (III) wherein R1 is chosen from linear $C_5$ and $C_7$ alkyl radicals.

14. The composition according to claim 13, wherein the at least one pigment is chosen from the red pigments of formula (III) wherein R2 is a residue derived from an amino acid.

15. The composition according to claim 14, wherein the at least one pigment is chosen from N-glutaryl monascorubramines, N-acetyl monascorubramines and N-acetyl rubropunctamines.

16. The composition according to claim 13, wherein the at least one pigment is chosen from rubropunctamine and monascorubramine.

17. The composition according to claim 1, wherein the at least one pigment is obtained by fermentation by culturing a strain chosen from *Monascus purpurea, Monascus ruber, Monascus major, Monascus rubiginosus, Monascus species*, and *Monascus anka*.

18. The composition according to claim 1, wherein the at least one pigment is an aqueous-alcoholic extract of *Monascus anka* sprayed onto maltodextrin (4 parts *Monascus anka*/96 parts maltodextrin).

19. The composition according to claim 1, wherein the at least one pigment is present in an amount ranging from 0.0001% to 10% by weight relative to the total weight of the composition.

20. The composition according to claim 19, wherein the at least one pigment is present in an amount ranging from 0.001% to 5% by weight relative to the total weight of the composition.

21. The composition according to claim 1, further comprising at least one self-tanning agent chosen from mono- and polycarbonyl self-tanning agents.

22. The composition according to claim 21, wherein the mono- and polycarbonyl self-tanning agents are chosen from isatin, alloxan, ninhydrin, glyceraldehyde, mesotartaricaldehyde, glutaraldehyde, erythrulose, pyrazoline-4,5-dione derivatives, dihydroxyacetone (DHA), and 4,4-dihydroxypyrazolin-5-one derivatives; these self-tanning agents possibly being combined with direct dyes or indole derivatives.

23. The composition according to claim 22, wherein the self-tanning agent is dihydroxyacetone (DHA).

24. The composition according to claim 21, wherein the at least one self-tanning agent is present in an amount ranging from 0.1% to 10% by weight relative to the total weight of the composition.

25. The composition according to claim 1, further comprising at least one agent chosen from organic agents and mineral agents for screening out UV radiation.

26. The composition according to claim 25, wherein the organic agents for screening out UV radiation are water-soluble, liposoluble, or insoluble in the usual cosmetic solvents.

27. The composition according to claim 26, wherein the organic agents for screening out UV radiation are chosen from anthranilates, cinnamic derivatives, dibenzoylmethane derivatives, salicylic derivatives, camphor derivatives, triazine derivatives, benzophenone derivatives, benzalmalonate derivatives, β,β'-diphenylacrylate derivatives, benzotriazole derivatives, benzimidazole derivatives, imidazolines, bis-benzazolyl derivatives, p-aminobenzoic acid (PABA) derivatives, methylenebis(hydroxyphenyl) benzotriazole derivatives, screening polymers and screening silicones, dimers derived from α-alkylstyrene, 4,4-diarylbutadiene derivatives, and mixtures thereof.

28. The composition according to claim 27, wherein the organic agents for screening out UV radiation are chosen from:
   Ethylhexyl salicylate,
   Butyl methoxydibenzoylmethane,
   Ethylhexyl methoxycinnamate,
   Octocrylene,
   Phenylbenzimidazolesulphonic acid,
   Terephthalylidenedicamphorsulphonic acid,
   Benzophenone-3,
   Benzophenone-4,
   Benzophenone-5,
   4-Methylbenzylidenecamphor,
   Disodiumphenyldibenzimidazole tetrasulphonate,
   Anisotriazine,
   Ethylhexyltriazone,
   Diethylhexylbutamidotriazone,
   2,4,6-tris(diisobutyl 4'-aminobenzalmalonate)-s-triazine,
   Methylenebis(benzotriazolyl)tetramethylbutylphenol,
   n-Hexyl 2-(4-diethylamino-2-hydroxybenzoyl)benzoate,
   1,1-dicarboxy(2,2'-dimethyl-propyl)-4,4-diphenylbutadienem
   Drometrizole trisiloxane,
   and mixtures thereof.

29. The composition according to claim 25, wherein the mineral agents for screening out UV radiation are chosen from coated and uncoated metal oxide pigments and nanopigments.

30. The composition according to claim 29, wherein the mineral agents for screening out UV radiation are chosen from coated and uncoated nanopigments of titanium oxide, of iron oxide, of zinc oxide, of zirconium oxide, and of cerium oxide.

31. The composition according to claim 25, wherein the at least one agent chosen from organic agents and mineral agents for screening out UV radiation is present in an amount ranging from 0.1% to 20% by weight relative to the total weight of the composition.

32. The composition according to claim 1, wherein said at least one pigment is different from an extract obtained from the mutant strain R300-30 of *Monascus anka* (FERM No. 11135).

33. The composition according to claim 1, wherein said at least one pigment is not linked to any of a regenerated silk fibroin powder, a porous magnesium silicate and a calcium aluminate silicate.

34. The composition according to claim 1, wherein the composition does not contain an ascorbic acid derivative or a retinol derivative.

35. A cosmetic process for treating skin to give said skin a long-lasting and non-covering coloration close to that of a natural tan comprising applying to said skin an effective amount of a composition comprising, in a cosmetically acceptable medium, at least one pigment, which may be obtained by extraction with a solvent chosen from organic and aqueous-organic solvents of a culture medium of *Monascus* micromycetes.

36. A cosmetic composition for giving skin a long-lasting and non-covering coloration close to that of a natural tan comprising, in said composition, a cosmetically acceptable medium and an effective amount of at least one pigment, which may be obtained by extraction with a solvent chosen from organic and aqueous-organic solvents of a culture medium of Monascus micromycetes.

37. A process for manufacturing a cosmetic and/or dermatological composition for giving skin a long-lasting and non-covering coloration close to that of a natural tan comprising including in the composition an effective amount of at least one pigment, which may be obtained by extraction with a solvent chosen from organic and aqueous-organic solvents of a culture medium of Monascus micromycetes.

* * * * *

UNITED STATES PATENT AND TRADEMARK OFFICE
CERTIFICATE OF CORRECTION

PATENT NO.     : 6,740,313 B2
DATED          : May 25, 2004
INVENTOR(S)    : Serge Forestier et al.

It is certified that error appears in the above-identified patent and that said Letters Patent is hereby corrected as shown below:

Column 15,
Line 24, "Mona scus" should read -- Monascus --.

Column 16,
Line 30, "diphenylbutadienem" should read -- diphenylbutadiene --.

Signed and Sealed this

Tenth Day of August, 2004

JON W. DUDAS
*Acting Director of the United States Patent and Trademark Office*